US00PP16228P3

(12) United States Plant Patent
Shaw et al.

(10) Patent No.: US PP16,228 P3
(45) Date of Patent: Jan. 31, 2006

(54) STRAWBERRY PLANT NAMED 'ALBION'

(50) Latin Name: *Fragaria×ananassa Duch.*
Varietal Denomination: Albion

(75) Inventors: Douglas V. Shaw, Davis, CA (US); Kirk D. Larson, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 99 days.

(21) Appl. No.: 10/769,471

(22) Filed: Jan. 29, 2004

(65) Prior Publication Data

US 2005/0172374 P1 Aug. 4, 2005

(51) Int. Cl.
*A01H 5/00* (2006.01)

(52) U.S. Cl. ..... Plt./209

(58) Field of Classification Search ..... Plt./209
See application file for complete search history.

*Primary Examiner*—Anne Marie Grunberg
*Assistant Examiner*—June Hwu
(74) *Attorney, Agent, or Firm*—Townsend and Townsend and Crew LLP

(57) ABSTRACT

This invention relates to a new and distinctive day-neutral type cultivar designated as 'Albion'. 'Albion' is a day-neutral (everbearing) cultivar similar to 'Diamante' (U.S. Plant Pat. No. 10,435), but with higher quality fruit, lower cull rate, darker fruit, and substantially better resistance to *Phytophthora cactorum;* it is similar to 'Aromas' (U.S. Plant Pat. No. 10,451), but with larger, higher quality, firmer and better-flavored fruit.

4 Drawing Sheets

Genus and species: The strawberry cultivar of this invention is botanically identified as *Fragaria×ananassa Duch.*

Variety denomination: The variety denomination is 'Albion'.

BACKGROUND OF THE INVENTION

'Albion' originated from a cross performed in 1997 between the cultivar 'Diamante' (U.S. Plant Pat. No. 10,435) and advanced selection Cal 94.16-1. 'Albion' was first fruited at the University of California Wolfskill Experimental Orchard, near Winters, Calif. in 1998, where it was selected, originally designated Cal 97.117-3, and propagated asexually by runners. Following selection and during testing, the plant was originally designated 'CN220', and subsequently has been named 'Albion' for introduction. Asexual propagules from this original source have been tested at the Watsonville Strawberry Research Facility, the South Coast Research and Extension Center, and to a limited extent in grower fields starting in 1999. The properties of this variety were found to be transmissible by such asexual reproduction. The cultivar is stable and reproduces true to type in successive generations of asexual reproduction.

BRIEF SUMMARY OF THE INVENTION

This invention relates to a new and distinctive day-neutral type cultivar designated as 'Albion'. 'Albion' is a day-neutral (everbearing) cultivar similar to 'Diamante' (U.S. Plant Pat. No. 10,435), but with higher quality fruit, lower cull rate, darker fruit, and substantially better resistance to *Phytophthora cactorum;* it is similar to 'Aromas' (U.S. Plant Pat. No. 10,451), but with larger, higher quality, firmer and better-flavored fruit.

BRIEF DESCRIPTION OF THE DRAWINGS

The figures depict various characteristics of the 'Albion' cultivar.

DETAILED DESCRIPTION OF THE INVENTION

Figure 1:
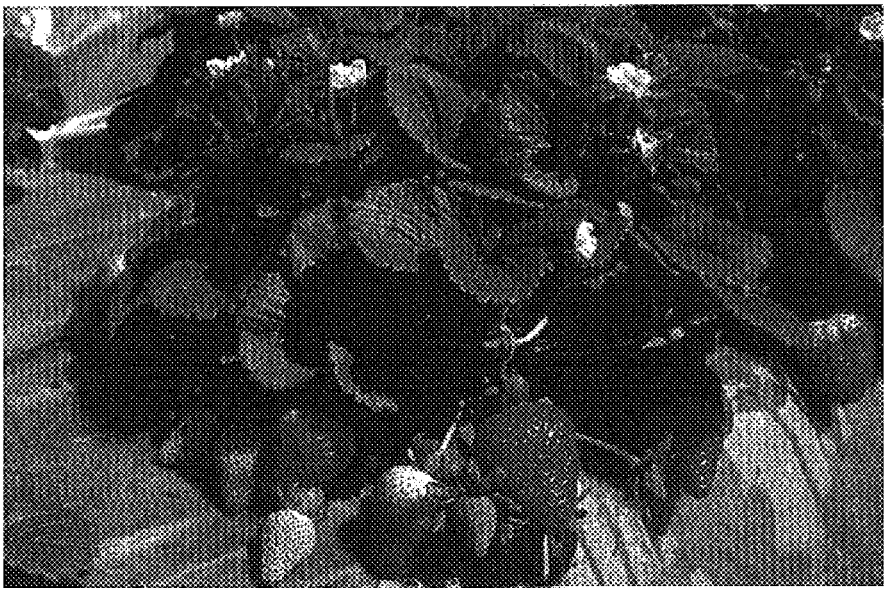
FIG. 1 shows the general flowering and fruiting characteristics of plants in a field planting.
Figure 2:
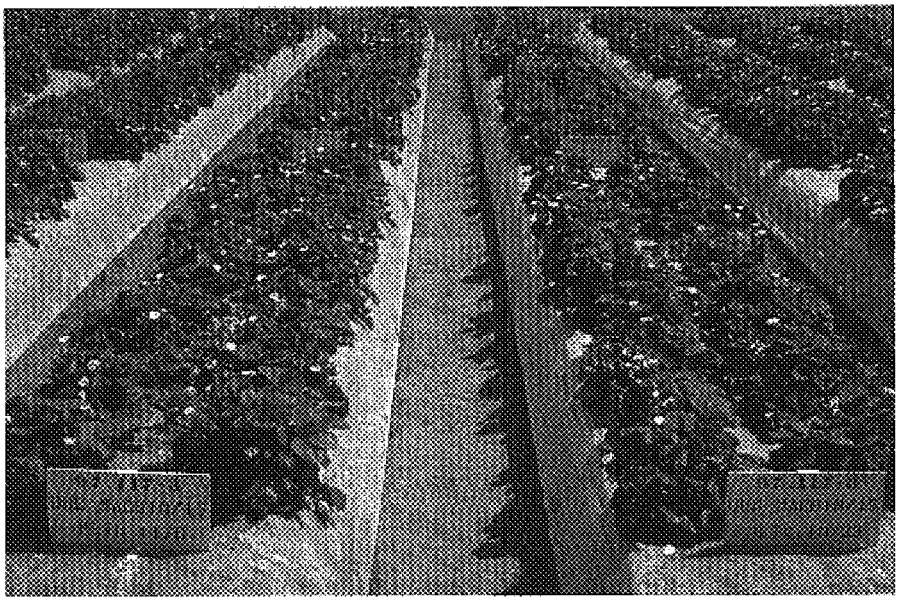
FIG. 2 shows rows of typical fruiting plants.
Figure 3:
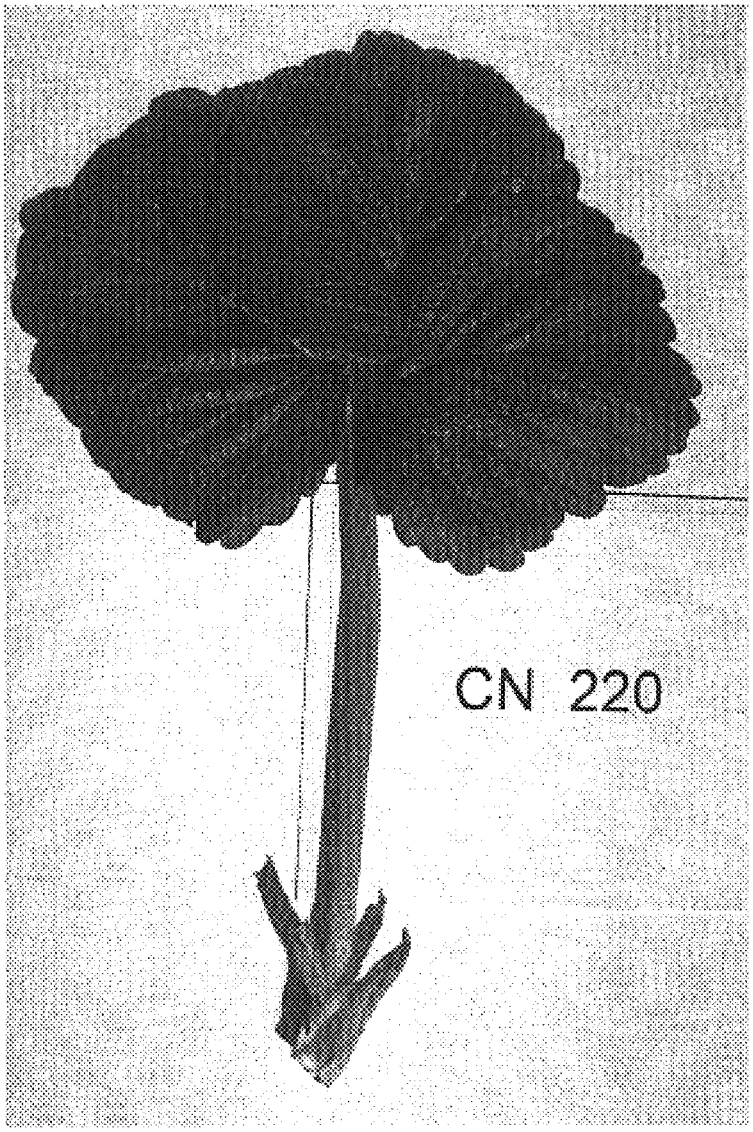
FIG. 3 shows a typical leaf at mid-season.
Figure 4:
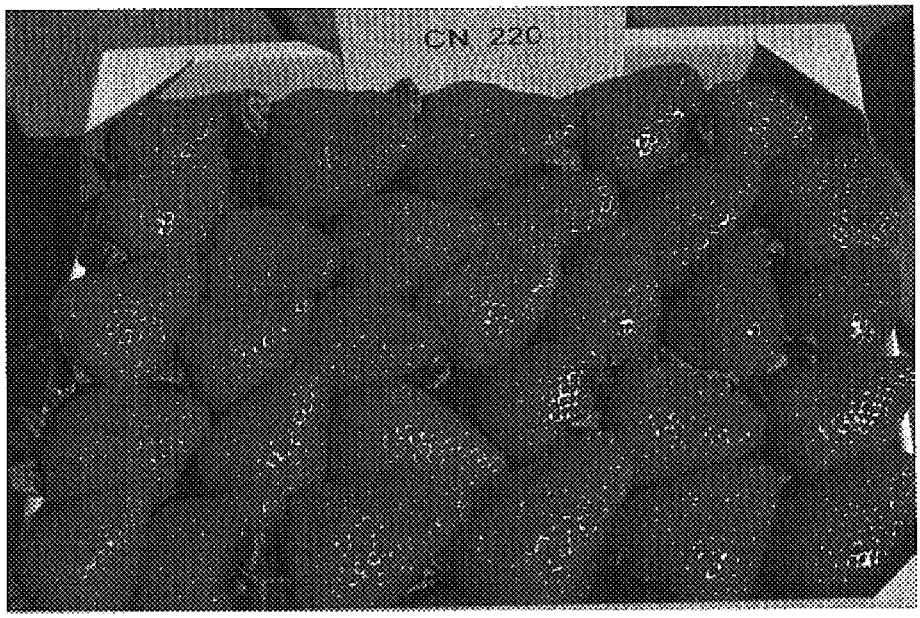
FIG. 4 shows representative mid-season fruit.

This invention relates to a new and distinctive day-neutral type cultivar designated as 'Albion'. 'Albion' is typical of day-neutral strawberry cultivars and produces fruit regardless of day length when treated appropriately in arid, subtropical climates. 'Albion' is moderate to weak in expressing the day-neutral character, being comparable to slightly more day-neutral than 'Diamante' (U.S. Plant Pat. No. 10,435), and less so than 'Fern' (U.S. Plant Pat. No. 5,267) or 'Irvine' (U.S. Plant Pat. No. 7,172). The production pattern for 'Albion' is similar to that for 'Diamante', although it is somewhat later to reach peak fruiting with most cultural treatments. 'Albion' will be of special interest for winter plantings and in summer plantings where 'Diamante' and 'Aromas' have been successful.

'Albion' has the following characteristics relative to parent 94.16-1. The 94.16-1 cultivar is a short-day or June-bearing genotype, whereas Albion is day-neutral. Albion has larger and more uniform sized fruit than 94.16-1, its fruit is substantially firmer, and better flavored. The fruit shape of 94.16-1 tends towards a short but symmetrical conic shape; Albion fruit has a long conical shape. Albion has substantially more even external fruit color, whereas 94.16-1 tends to be mottled during some portions of the season.

Plants and foliage: Fruiting plants of 'Albion' are similar in morphology to 'Diamante' although slightly more erect and more open; 'Albion' plants are substantially more open and erect than 'Aromas' plants. Comparative statistics for foliar characters near mid-season are given for 'Albion' and the two comparison cultivars in Table 1. Individual leaflets for 'Albion' are smaller than for 'Aromas' or 'Diamante', and somewhat less rounded than for 'Diamante'. Leaves (including petioles) for 'Albion' are shorter than those for the comparison cultivars, mostly due to shorter petiole length. Petioles are generally thicker than those of the comparison cultivars and tend to have heavy pubescence. The adaxial (upper) and abaxial (lower) surfaces of leaves for 'Albion' are similar in color to 'Aromas' and 'Diamante' leaves at mid season, but tend to remain darker and less yellow than those of either comparison cultivar late in the harvest season. Leaves of 'Albion' have consistently less concavity than 'Aromas', and are similar in form to 'Diamante', with more, and usually more rounded serrations than the comparison cultivars.

TABLE 1

Foliar characteristics for 'Albion', 'Aromas', and 'Diamante'.

| Foliar | Cultivar | | |
|---|---|---|---|
| Character | 'Aromas' | 'Diamante' | 'Albion' |
| Plant height (mm) | | | |
| mean | 257 | 231 | 252 |
| range | 230–330 | 160–275 | 210–270 |
| Plant spread (mm) | | | |
| mean | 318 | 357 | 341 |
| range | 241–382 | 292–419 | 304–394 |
| Mid-tier leaflet | | | |
| Length (mm) | | | |
| mean | 92 | 77 | 73 |
| range | 67–100 | 55–110 | 50–95 |
| Width (mm) | | | |
| mean | 74 | 81 | 68 |
| range | 65–85 | 55–110 | 50–95 |
| Mid-tier leaf | | | |
| Length (mm) | | | |
| mean | 253 | 215 | 185 |
| range | 172–305 | 169–290 | 153–223 |
| Width (mm) | | | |
| mean | 156 | 149 | 135 |
| range | 135–200 | 90–210 | 105–170 |
| Leaf components | | | |
| Petiole length (mm) | | | |
| mean | 154 | 126 | 105 |
| range | 100–225 | 92–170 | 70–130 |
| Petiole diameter (mm) | | | |
| mean | 3.6 | 3.7 | 4.1 |
| range | 3.0–4.2 | 3.0–4.8 | 3.7–4.6 |
| Petiolule length (mm) | | | |
| mean | 7.2 | 11.4 | 7.4 |
| range | 7–12 | 8–15 | 5–10 |
| # leaflets/leaf | 3 | 3 | 3 |
| Leaf convexity | some flat, most slight concave | some flat, most slight concave | some flat, most slight concave |
| Serrations | | | |
| number/leaf | 65.1 | 63.1 | 71.8 |
| range | 57–71 | 45–72 | 55–87 |
| shape | semi-pointed | semi-pointed | semi-pointed |

TABLE 1-continued

Foliar characteristics for 'Albion', 'Aromas', and 'Diamante'.

| Foliar | Cultivar | | |
|---|---|---|---|
| Character | 'Aromas' | 'Diamante' | 'Albion' |
| Leaf pubescence | moderate | very light | light-moderate |
| Petiole pubescence | | | |
| density | moderate | moderate to heavy | heavy |
| direction | perpendicular | perpendicular to slightly acropetal | perpendicular |
| Petiole color (Munsell) | 5GY 6/8 | 5GY 6/8<br>5GY 7/10 | 5GY 7/10 |
| Stipule length (mm) | | | |
| mean | 26.9 | 26.5 | 23.3 |
| range | 25–31 | 20–35 | 14–34 |
| Stipule color | | | |
| core | 5GY 6/8 | 5GY 6/8 | 5GY 6/8 |
| margins | 2.5R 7/8 | 2.5R 6/11 | 2.5R 7/8 |
| Stolons per nursery mother plant | 30.3 | 24.4 | 22.5 |
| Venation pattern | pinnate | pinnate | pinnate |
| color | 2.5GY 6/8 | 2.5GY 6/8 | 2.5GY 6/8 |

Flowering, fruiting, fruit, and production characteristics: 'Albion' is similar to other California day-neutral cultivars (e.g., 'Diamante' and 'Aromas') in that it will flower independently of day length, given appropriate temperature and horticultural conditions. Comparative statistics for flower and fruit characters near mid-season are given for the three cultivars in Table 2. The primary flowers for 'Albion' are similar in size to 'Diamante' and larger than those of 'Aromas'; the sepals are similar in length to both comparison cultivars, but intermediate in width. The calyx for 'Albion' varies in position but is more frequently slightly necked than either comparison cultivar; each primary flower has 5–8 petals.

The habit is semi-erect to prostrate, usually semi-erect. The relative position of the inflorescence to the leaves is exposed, or above the foliage.

TABLE 2

Flower and fruit characters for 'Albion', 'Diamante', and 'Aromas'.

| | Cultivar | | |
|---|---|---|---|
| Character | 'Aromas' | 'Diamante' | 'Albion' |
| Petal number | | | |
| mean | 5.7 | 5.4 | 6.0 |
| range | 5–7 | 5–6 | 5–8 |
| Petal shape | | | |
| apex | truncate to slightly obtuse | truncate to slightly obtuse | truncate to slightly obtuse |
| base | attenuate | attenuate | attenuate |
| margin | entire | entire | entire |
| Petal length (mm) | | | |
| mean | 13.8 | 13.4 | 12.7 |
| range | 12–16 | 11–17 | 11–15 |

TABLE 2-continued

Flower and fruit characters for 'Albion', 'Diamante', and 'Aromas'.

| Character | Cultivar 'Aromas' | 'Diamante' | 'Albion' |
|---|---|---|---|
| Petal width (mm) | | | |
| mean | 13.6 | 13.2 | 12.6 |
| range | 11–16 | 12–15 | 11–14 |
| Flower position (relative to foliage) | most even some internal | most even some internal and exposed | most exposed, some even |
| Calyx diam. (mm) | | | |
| mean | 28.6 | 35.2 | 35.8 |
| range | 27–30 | 24–40 | 30–39 |
| Corolla diam. (mm) | | | |
| mean | 26.3 | 28.8 | 27.0 |
| range | 23–28 | 21–34 | 25–30 |
| Sepal length (mm) | | | |
| mean | 15.8 | 19.1 | 18.5 |
| range | 15–19 | 13–25 | 14–24 |
| Sepal width (mm) | | | |
| mean | 5.8 | 9.5 | 7.1 |
| range | 4–8 | 7–16 | 5–9 |
| Sepal color (Munsell) | 5GY 5/6 | 5GY 5/6 | 7.5GY 4/4 |
| Pedicel length (mm) | | | |
| mean | 129.5 | 148.2 | 113.0 |
| range | 110–160 | 110–180 | 83–190 |
| Pedicel diameter (mm) | | | |
| mean | 2.4 | 2.3 | 2.9 |
| range | 1.9–3.3 | 1.8–2.7 | 2.2–3.5 |
| Pedicel color | 5GY 6/8 | 2.5GY 6/8 | 5GY 6/8 |
| Fruit shape | | | |
| Fruit length (mm) | | | |
| mean | 48.4 | 53.5 | 60.6 |
| range | 45–57 | 45–60 | 55–75 |
| Fruit width (mm) | | | |
| mean | 43.7 | 51.1 | 49.7 |
| range | 35–50 | 45–60 | 45–55 |
| Length/width | | | |
| ratio | 1.1 | 1.0 | 1.2 |
| range | 0.9–1.3 | 0.9–1.3 | 1.1–1.4 |
| subjective | mostly medium to short rounded conic | rounded to flat conic | most long symmetrical conic |
| Calyx position | even to indented | even to indented | even to slight neck |
| Seed position | even to indented | mostly indented, some even | mostly indented, some even |

The fruit shape for 'Albion' can vary but is typically a long and symmetrical conic, and is easily distinguished from 'Aromas' (shortened and rounded conic) or 'Diamante' (rounded and occasionally flattened conic); 'Albion' usually has a greater proportion of symmetrical fruit than either comparison cultivar. External and internal fruit color for 'Albion' is darker than for 'Diamante' and slightly lighter than for 'Aromas' with substantially greater red color (Table 3). Achenes vary from yellow to dark red (Table 3), and are even with the fruit surface or slightly indented. The mean number of achenes per berry is 440.8 (range of 330–548). The average berry weight is 33 grams (Table 4). The adherence of the calyx to the fruit is medium. The hollow portion of the fruit interior generally ranges from about 0–15%, subjectively, and is variable with culture and season.

'Albion' is substantially sweeter than 'Diamante' throughout the season, but has moderate acid levels as well. Average brix was 8.5 and average acidity was 0.74 for two evaluations performed on two dates in 2003.

Secondary fruit is similar in shape to primary fruit and is generally about 75%, subjectively, of the size, although this is variable through the season and with culture conditions. Calyx for secondary fruit can vary from slightly larger than the berry to slightly smaller, depending on the season.

TABLE 3

Foliar and fruit color characteristics for 'Albion', 'Aromas', and 'Diamante'.

| Color Character | Cultivar 'Aromas' | 'Diamante' | 'Albion' |
|---|---|---|---|
| Leaf color (CIELAB) | | | |
| Adaxial | | | |
| L* | | | |
| mean | 32.7 | 32.4 | 32.7 |
| range | 31.1–34.2 | 29.9–35.8 | 31.5–34.1 |
| a* | | | |
| mean | −7.0 | −8.1 | −7.4 |
| range | −5.8—8.2 | −7.3—10.2 | −6.3—8.1 |
| b* | | | |
| mean | 11.8 | 12.0 | 11.7 |
| range | 9.6–14.0 | 9.1–13.9 | 10.4–13.1 |
| Munsell | 2.5GY 3/3 | 10GY 3/2 | 5GY 3/2 |
| Abaxial | | | |
| L* | | | |
| mean | 52.3 | 50.7 | 49.1 |
| range | 34.1–52.3 | 48.3–52.4 | 48.6–52.1 |
| a* | | | |
| mean | −8.3 | −9.0 | −8.8 |
| range | −6.8—8.8 | −8.4—9.5 | −7.6—9.2 |
| b* | | | |
| mean | 18.1 | 19.1 | 19.3 |
| range | 13.1–20.1 | 17.9–21.3 | 15.7–21.6 |
| Munsell | 5GY 5/6 7.5GY 5/7 | 5GY 5/6 | 5GY 5/6 |
| Fruit color (CIELAB) | | | |
| External | | | |
| L* | | | |
| mean | 38.1 | 43.7 | 40.0 |
| range | 36.6–41.4 | 39.5–47.4 | 34.3–44.8 |
| a* | | | |
| mean | 39.3 | 41.7 | 41.2 |
| range | 37.3–41.2 | 35.0–46.3 | 34.8–44.2 |
| b* | | | |
| mean | 27.2 | 32.1 | 28.4 |
| range | 21.7–32.9 | 27.0–35.9 | 20.9–36.9 |
| Munsell | 5R 3/7 | 7.5R 4/11 | 5R 3/7 |
| Internal | | | |
| L* | | | |
| mean | 65.1 | 68.3 | 63.2 |
| range | 56.4–70.6 | 63.7–71.1 | 56.3–64.4 |

TABLE 3-continued

Foliar and fruit color characteristics for 'Albion', 'Aromas', and 'Diamante'.

| Color Character | Cultivar 'Aromas' | 'Diamante' | 'Albion' |
|---|---|---|---|
| a* | | | |
| mean | 31.2 | 23.9 | 31.1 |
| range | 13.3–40.3 | 15.5–30.6 | 20.1–35.9 |
| b* | | | |
| mean | 34.5 | 29.2 | 33.1 |
| range | 17.1–41.7 | 20.3–35.9 | 24.0–35.9 |
| Munsell | 5R 4/12 | 7.5R 6/12 | 7.5R 4/11 |
| Achene color | | | |
| Munsell | 7.5R 3/6 | 7.5R 3/6 | 7.5R 3/6 |

*CIELAB is the abbreviation of the international color system known as "Commission Internationale De L'Eclairage" 1978. For recommendations concerning uniform color spaces, color difference equations, and psychometric color terms see Supplement No. 2 of CIE Publication No. 15, Paris.

'Albion' has been tested under a variety of cultural regimes, and optimal performance is obtained when nursery treatments and nutritional programs similar to those for 'Diamante' are used. In general, 'Albion' is very similar in vigor to 'Diamante' and requires less chilling to maintain excellent fruit quality than 'Aromas'. 'Albion' retains good fruit quality in summer planting systems, similar to 'Diamante'.

It is possible that the phenotype may vary somewhat with variations in the environment. Phenotypic features may also vary depending on culture conditions.

When treated with appropriate planting regimes, 'Albion' has similar fruit size and produces similar individual-plant yields to 'Diamante'; it produces less per plant but develops higher quality fruit than 'Aromas' (Table 4). 'Albion' has a similar production pattern to 'Diamante', although the production is less peaked and less affected by yearly variation in climate. The following is an exemplary flowering and fruiting schedule for Watsonville, Calif. These exemplary times are based on planting runners in fruiting fields during the first part of November (November 1–10). Initiation of flowering depends on the weather. It may occur as little as 6 week after planting and is typically around 3 to 4 months (February 1 to March 20). Termination of flowering is temperature dependent and day-length independent for this cultivar. From flowering to ripe fruit takes as long as 7 weeks in the short days and cool temperatures of winter, as little as 3 weeks in summer. First fruit is typically available April 1–May 15 for this example.

Commercial appearance ratings have been better than those for 'Diamante' and substantially better than those for 'Aromas'; these superior appearance scores translate directly into a smaller fraction of non-marketable fruit than is produced by the comparison cultivars. Fruit for 'Albion' is substantially firmer than fruit from 'Aromas', slightly less firm than 'Diamante'. Subjectively, 'Albion' has outstanding flavor. The fruit will be exceptional for both fresh market and processing, and will be useful for home garden purposes.

TABLE 4

Performance of 'Albion', 'Aromas', and 'Diamante' evaluated at the Watsonville Research Facility in 2001 and 2002. All plants for these trials were harvested from Macdoel on October 15, and transplanted after 20–28 days supplemental storage. Harvest was initiated in early April and continued through the last week of October. Late yield is that accumulated after August 15 (52" 2-row beds, 17,300 plants/acre).

| Item | Yield (g/plant) | Late Yield (g/plant) | Appearance Score (5 = best) | Fruit Size (g/fruit) | Firmness* |
|---|---|---|---|---|---|
| 'Aromas' | 2,762 | 582 | 3.3 | 28.0 | 8.6 |
| 'Diamante' | 2,346 | 456 | 3.6 | 33.5 | 9.8 |
| 'Albion' | 2,417 | 522 | 4.0 | 33.0 | 9.3 |

*Fruit firmness ratings are the amount of force in tenths of pounds required to drive a 3 mm flat probe 1 cm into a ripe fruit. This is measured with a Hunter Force Gauge.

Disease and pest reaction: 'Albion' is moderately resistant to common leaf spot (*Ramularia tulasnei*) and powdery mildew (*Sphaerotheca macularis*). It is quite resistant to *Verticillium* wilt (*Verticillium dahliae*) and *Phytophthora* crown rot (*Phytophthora cactorum*), and moderately resistant to Anthracnose crown rot (*Colletotrichum acutatum*) (Table 5). When treated properly, it has tolerance to two-spotted spider mites (*Tetranychus urticae*) equal to that for 'Diamante' and better than that for 'Aromas'. 'Albion' is tolerant to strawberry viruses encountered in California.

TABLE 5

Disease resistance scores for 'Albion', 'Aromas', and 'Diamante'; *Phytophthora* and *Verticillium* scores were obtained in evaluations conducted in 2000–2003, *Colletotrichum* was evaluated in 2003.

| Genotype | *Phytophthora* Resistance Score (5 = best) | *Verticillium* Resistance Score (5 = best) | *Colletotrichum* Resistance Score (5 = best) |
|---|---|---|---|
| 'Aromas' | 4.2 | 3.5 | 2.7 |
| 'Diamante' | 2.4 | 2.7 | 2.6 |
| 'Albion' | 4.9 | 3.4 | 3.1 |

What is claimed is:

1. A new and distinct cultivar of strawberry plant having the characteristics substantially as described and illustrated herein.

* * * * *